United States Patent [19]

Heitmann

[11] Patent Number: 4,616,139
[45] Date of Patent: Oct. 7, 1986

[54] APPARATUS FOR OPTICAL SCANNING OF THE EXTERIOR OF A MOVING CIGARETTE ROD OR THE LIKE

[75] Inventor: Uwe Heitmann, Hamburg, Fed. Rep. of Germany

[73] Assignee: Hauni-Werke Körber & Co. KG., Hamburg, Fed. Rep. of Germany

[21] Appl. No.: 613,899

[22] Filed: May 24, 1984

[30] Foreign Application Priority Data

May 31, 1983 [DE] Fed. Rep. of Germany ....... 3319691

[51] Int. Cl.⁴ .......................... G01N 21/88; B07C 5/00
[52] U.S. Cl. .................................... 250/572; 131/905; 209/536
[58] Field of Search ................ 209/535, 536; 131/905, 131/906, 907, 908, 910, 84 R; 250/562, 563, 572, 571

[56] References Cited

U.S. PATENT DOCUMENTS

| | | | |
|---|---|---|---|
| 3,914,989 | 10/1975 | Reuland et al. | 73/69 |
| 4,037,608 | 7/1977 | Wahle | 131/21 B |
| 4,208,578 | 6/1980 | McLoughlin et al. | 209/536 |
| 4,215,939 | 8/1980 | Miller et al. | 250/572 |
| 4,350,170 | 9/1982 | Baier | 131/84 R |
| 4,377,743 | 3/1983 | Bolt et al. | 209/536 |

FOREIGN PATENT DOCUMENTS

| | | | |
|---|---|---|---|
| 56-40744 | 4/1981 | Japan | 250/563 |
| 807785 | 1/1959 | United Kingdom | 131/906 |

Primary Examiner—David C. Nelms
Assistant Examiner—Michael Messinger
Attorney, Agent, or Firm—Peter K. Kontler

[57] ABSTRACT

A portion of the path for a moving cigarette or filter rod in a cigarette rod making or filter rod making machine is surrounded by a ring-shaped carrier for a polygonal light-transmitting rod guide and a set of radiation conducting units, one behind each facet of the guide. Each unit receives a beam of radiation from a discrete source and directs such radiation radially of and at right angles to the axis of the moving rod. Radiation which is reflected by the exterior of the rod is caused to pass through the respective unit and is directed against a discrete photoelectric transducer which generates signals denoting the characteristics of reflected radiation. Such signals are used to evaluate the condition of the exterior of the rod and, if necessary, for segregation of corresponding (defective) plain cigarettes or filter rod sections from satisfactory cigarettes or filter rod sections.

16 Claims, 4 Drawing Figures

APPARATUS FOR OPTICAL SCANNING OF THE EXTERIOR OF A MOVING CIGARETTE ROD OR THE LIKE

BACKGROUND OF THE INVENTION

The present invention relates to improvements in apparatus for monitoring the external surfaces of moving objects, and more particularly to improvements in apparatus for optical scanning or monitoring of the exterior of moving rod-shaped commodities, such as cigarette rods, filter rods and other rod-shaped products of the tobacco processing industry. Still more particularly, the invention relates to improvements in optical scanning apparatus of the type wherein radiation is directed against the external surface of a moving rod and the radiation which is reflected by the external surface of the rod is evaluated in order to ascertain the condition of monitored portions of the external surface.

Defects in the wrappers of rod-shaped products of the tobacco processing industry cause more or less pronounced changes in the characteristics of light or other types of radiation which is reflected by the external surfaces of such products. For example, a hole in the wrapper of a cigarette rod or filter rod will cause a pronounced change in the intensity of reflected radiation and such changes can be detected by photoelectric transducers to generate signals which are indicative of fluctuations of the reflected radiation. The signals can be evaluated and used, for example, to segregate defective rod-shaped articles from satisfactory articles. Analogously, adhesive spots or printed matter on the wrappers of cigarette rods or the like reflect radiation differently than the remaining portions of the external surface of the wrapper of a cigarette rod, filter rod or the like. The presence of a hole in the wrapper of a cigarette rod entails a reduction of the intensity of reflected radiation because the effect of the hole is the same as that of a dark spot on the normally white cigarette paper. On the other hand, a spot of glue on the exterior of the wrapper of a cigarette rod entails a more pronounced reflection of impinging radiation so that the presence of such adhesive spot can be detected by converting reflected radiation into a signal of more pronounced intensity than anticipated for the scanning of a satisfactory portion of the wrapper. In this manner, an optical scanning system can ascertain the presence or absence of a variety of defects including holes in the wrappers, the absence or improper application of imprints, the presence or absence of adhesive spots, smudges and/or a combination of the above. Moreover, such optical scanning systems can also be used to ascertain whether or not an imprint is sufficiently dark or is applied in the proper color because the extent of reflection of radiation by an imprint which is applied to the exterior of a wrapper consisting of cigarette paper or the like fluctuates or varies in dependency on the tone or shade of the coloring agent which is used for the application of imprints. In other words, by properly evaluating the reflected radiation, a suitable electronic or other evaluating system can categorize the defects and can generate signals which are then used for segregation of defective smokers' products from satisfactory products if the intensity of signals denoting particular defects is sufficiently pronounced or sufficiently low to warrant such segregation.

U.S. Pat. No. 4,350,170 granted Sept. 21, 1982, to Baier discloses an apparatus for monitoring the exterior of a moving cigarette rod or the like. The patented apparatus employs a ring-shaped light-conducting prism which is mounted in an annular housing surrounding a portion of the path for a moving cigarette rod or the like. The prism is designed to direct light at an acute angle to the axis of the moving rod, and the light which is reflected by the exterior of the moving rod passes through an annulus of light-conducting fibers each of which directs reflected light against a discrete photoelectronic transducer. Signals which are generated by the transducers are evaluated and utilized for segregation of defective cigarettes from satisfactory products. In addition, such signals can be utilized to adjust the machine which turns out the rod so as to ensure that the defects which happen to recur at frequent intervals or continuously can be eliminated with little loss of time.

An advantage of the patented apparatus is that, due to impingement of light at an acute angle to the axis of the moving rod, such apparatus can increase the contrast between the signals which are indicative of satisfactory and unsatisfactory portions of the exterior of the moving rod. In other words, this apparatus can ascertain the presence of pronounced as well as smaller defects with a high degree of reliability. However, the patented apparatus also exhibits a drawback, namely that light beams which are directed against the exterior of the moving rod at an acute angle to the axis of the rod cause the development of pronounced shadows as a result of detection of folds or undulations in the wrapping material which are not necessarily indicative of unsatisfactory portions of the wrappers but are interpreted as such by the evaluating system of the patented apparatus so that the corresponding rod-shaped articles are segregated even though their wrappers are satisfactory for further processing (such as packing) of the corresponding articles.

OBJECTS AND SUMMARY OF THE INVENTION

An object of the invention is to provide an apparatus which can be utilized for selective scanning of the exterior of a moving cigarette rod or the like in such a way that the apparatus generates defect signals only when warranted by the quality of the monitored portion of the wrapper.

Another object of the invention is to provide an apparatus which can discriminate between genuine defects and those which, in conventional apparatus, are classified as full-fledged defects exclusively due to particular orientation of incident radiation with reference to the moving product.

A further object of the invention is to provide an apparatus which can reliably segregate rod-shaped articles containing defective wrappers but can also reliably prevent segregation of articles which would be segregated in a conventional apparatus solely due to the peculiarities of construction and/or mode of operation of the testing apparatus.

An additional object of the invention is to provide an apparatus which can generate signals of desired intensity so as to facilitate the evaluation of such signals by a relatively simple electric circuit or the like.

Still another object of the invention is to provide a novel and improved method of detecting holes, spots of adhesive, improperly applied imprints, the absence of imprints, improperly colored imprints, smudges, open seams and/or combinations of two or more such defects in each and every portion of the exterior of a continuously or intermittently moving rod containing tobacco and/or filter material.

A further object of the invention is to provide a relatively simple and compact apparatus which can be installed in existing cigarette rod making, filter rod making and analogous machines as a superior substitute for heretofore used monitoring apparatus.

An additional object of the invention is to provide the apparatus with novel and improved means for directing radiation toward and for directing reflected radiation away from the exterior of a moving cigarette rod or the like.

The invention is embodied in an apparatus for optically scanning or monitoring the exterior of cigarette rods and analogous rod-shaped products of the tobacco processing industry which move lengthwise along a predetermined path. The apparatus comprises a plurality of radiation conducting units which at least partially surround a portion of the path for the moving rod and serve to conduct radiation substantially radially inwardly toward and at right angles to the axis of the rod, means for admitting radiation to the conducting units so that such radiation is directed against the corresponding portions of the exterior of the moving rod and is reflected back into the respective units whereby the characteristics of reflected radiation indicate or denote the condition of the corresponding portion of the exterior of the rod, and means for generating signals denoting the characteristics of reflected radiation.

The radiation conducting units can form an annulus around the rod in the aforementioned portion of the path for the moving rod, and such apparatus preferably further comprises carrier means for the radiation conducting units. The radiation admitting means can comprise at least one radiation source, and the signal generating means can comprise at least one photoelectrical transducer. For example, the radiation admitting means can comprise a discrete light source for each radiation conducting unit, and the signal generating means can comprise a discrete transducer for each radiation conducting unit. Each of these units can comprise at least one mirror and at least one lens.

The aforementioned carrier means can comprise an annular carrier for the radiation conducting units, and the carrier surrounds the rod in the aforementioned portion of the path. Such apparatus preferably further comprises a radiation-transmitting rod guide which is installed in the carrier and is interposed between the radiation conducting units and the rod in the aforementioned portion of the path so that radiation which issues from the admitting means as well as the radiation which is reflected by the exterior of the rod passes through the rod guide. Such guide can comprise a sleeve, for example a hollow cylindrical sleeve.

The rod guide preferably comprises a radiation transmitting plate for each radiation conducting unit. Such plates can form a polygonal sleeve, and each plate is disposed in a plane which extends at right angles to the direction of propagation of radiation from the respective unit to the corresponding portion of the exterior of the rod in the aforementioned portion of the path and also to the direction of propagation of reflected radiation back to the respective radiation conducting unit.

As mentioned above, the radiation admitting means can comprise a discrete radiation source which admits a light beam to the respective unit, and each such unit can include a beam splitting means which serves to direct a portion of the respective beam of radiation against the exterior of the rod in the aforementioned portion of the path and a portion of the reflected radiation against the signal generating means, normally against the corresponding photoelectric transducer. Such beam splitting means can comprise partly transmitting mirrors.

In accordance with a presently preferred embodiment of the invention, each of the radiation conducting units can comprise a totally reflecting mirror which serves to direct radiation from the respective source substantially radially toward the exterior of the rod in the aforementioned portion of the path, and a partially transmitting mirror which is disposed in the path of radiation from the respective totally reflecting mirror and serves to direct a portion of reflected radiation toward the signal generating means. In such apparatus, the units can be uniformly distributed around the rod in the aforementioned portion of the path, and the apparatus can further comprise an annular carrier for such units as well as for the aforementioned light-transmitting rod guide which is installed in the carrier between the partially transmitting mirrors and the rod so as to permit passage of radiation from the partially transmitting mirrors to the exterior of the rod as well as the passage of reflected radiation to the partially transmitting mirrors.

The apparatus can also comprise a discrete diaphragm for each radiation conducting unit. Such diaphragms serve for controlled transmission of radiation from the admitting means to the exterior of the rod as well as for controlled transmission of reflected radiation to the signal generating means.

It is often preferred to install the radiation sources on the optical axes of the respective radiation transmitting units in such a way that the sources are movable along such optical axes. The same applies for the transducers, i.e., each transducer is preferably adjustable along the optical axis of the corresponding radiation transmitting unit. The adjustable radiation sources and/or the adjustable transducers can be mounted on or in the carrier of the radiation conducting units.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENTS

Figure 1:
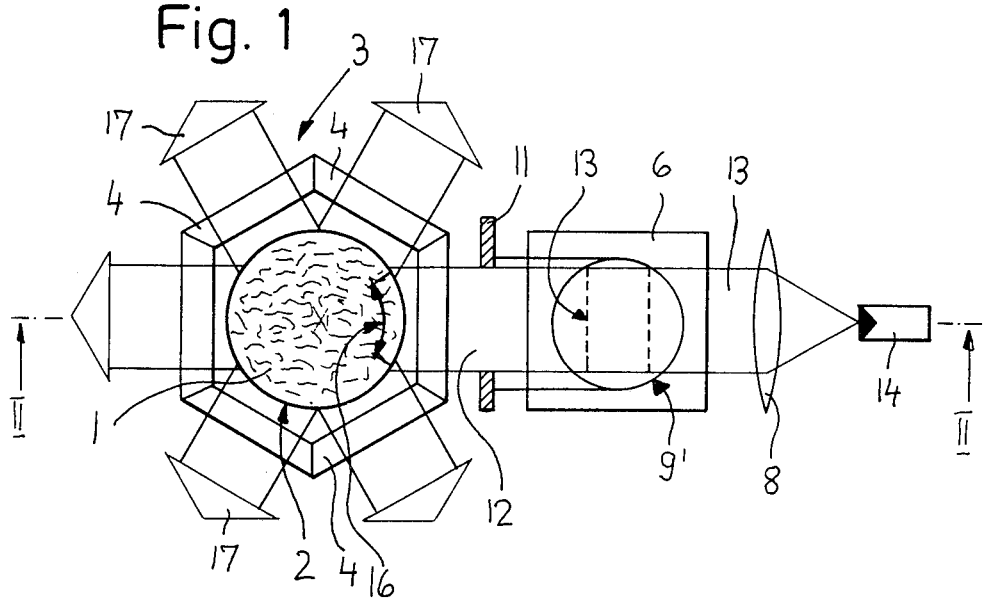
FIG. 1 is a schematic transverse sectional view of a moving cigarette rod and a partly schematic end elevational view of a scanning or monitoring apparatus which embodies one form of the invention.
Figure 2:
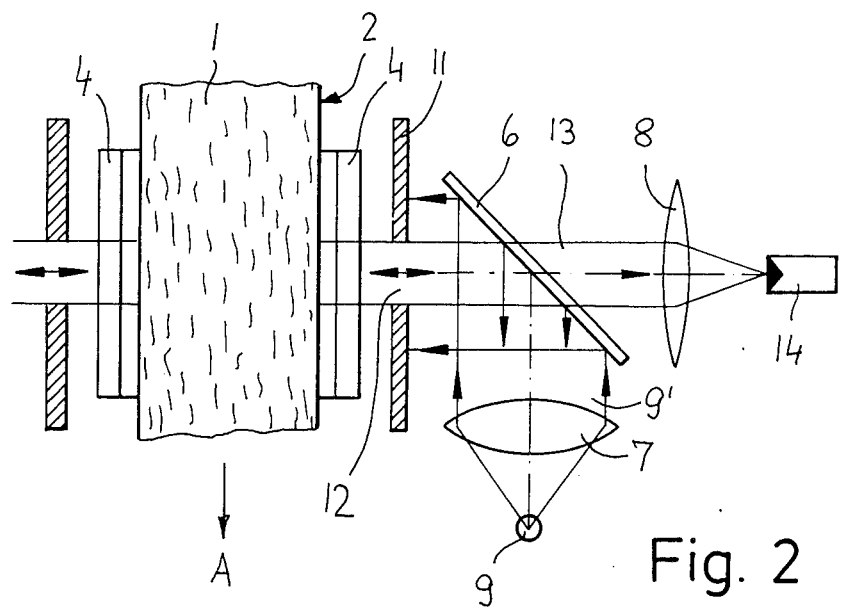
FIG. 2 is a schematic sectional view as seen in the direction of arrows from the line II—II of FIG. 1.

Referring first to FIGS. 1 and 2, there is shown a scanning or monitoring apparatus which is constructed in accordance with the present invention. These Figures merely show those components of the improved apparatus which are necessary for proper understanding of the invention as well as for proper visualization of their mutual positions.

The reference character 1 denotes a cigarette rod which is moved axially in the direction indicated by the arrow A, for example, in a cigarette rod making machine on its way toward the customary cutoff which subdivides the rod into plain cigarettes of unit length or multiple unit length. A cigarette rod making machine in which the apparatus of the present invention can be put to use is disclosed, for example, in commonly owned U.S. Pat. No. 4,037,608 granted July 26, 1977 to Wahle. The rod 1 has a cylindrical wrapper or envelope 2 which consists of cigarette paper or other suitable wrapping material. The purpose of the improved scanning apparatus is to detect the presence or absence of holes, open seams, smudges, improperly applied or colored imprints, the presence or absence of imprints, pronounced irregularities in the shape of the rod and/or a combination of such defects. Moreover, the apparatus can ascertain the presence or absence of adhesive spots at the exterior of the wrapper 2.

The cigarette rod 1 is caused to advance along an elongated path which can but need not be horizontal and a portion of which is surrounded by an annular rod guide 3 which, in the embodiment of FIGS. 1 and 2, consists of six identical light-transmitting plates 4 together forming a polygonal sleeve having six identical sides and spacedly surrounding the wrapper 2 of the moving rod 1. The planes of the plates 4 are disposed at right angles to imaginary lines which intersect at right angles the axis of the moving rod 1. The rod guide 3 is installed in a ring-shaped carrier 18 (see FIG. 3) which is not shown in FIGS. 1 and 2 for the sake of clarity.

The improved optical scanning apparatus comprises six radiation conducting units, one for each light transmitting plate 4 of the rod guide 3. The details of one such unit are shown in the right-hand portions of FIGS. 1 and 2. Each of the radiation conducting units comprises a partially light transmitting mirror 6 and two collector lenses 7 and 8. The radiation admitting means of the improved apparatus comprises six light sources 9, each of which is disposed in the focal point of the respective collector lens 7 so as to direct radiation against one side of the corresponding mirror 6. The mirror 6 reflects a portion of radiation radially toward the exterior of the moving rod 1 whereby such radiation passes through the slot 12 of a slotted diaphragm 11 which defines that beam of radiation that can actually impinge upon the exterior of the wrapper 2 after having passed through the corresponding plate 4 of the rod guide 3. The exterior of the wrapper 2 reflects radiation to a variable extent, and such reflected radiation passes again through the slot 12 of the diaphragm 11 and a portion thereof is permitted to pass through the mirror 6 so as to reach the collector lens 8 which focuses reflected radiation upon the photosensitive portion of an optoelectrical transducer 14. The latter generates signals whose intensity or another characteristics is proportional to, and hence indicative of, the characteristics of reflected radiation. The characteristics of such radiation are indicative of the condition or quality of the corresponding portions of the wrapper 2. The arrangement is such that radiation which is deflected by the mirror 6 to pass through the slot 12 of the diaphragm 11 and to impinge upon the exterior of the wrapper 2 passes at right angles to the plane of the corresponding plate 4 and at right angles to the axis of the moving rod 1. The light-sensitive portion of the transducer 14 is located in the focal point of the collector lens 8. The optical scanning apparatus of FIGS. 1 and 2 is capable of reliably generating signals which are truly indicative of the condition of monitored portions of the wrapper 2, and such signals can be evaluated to classify the detected defects and/or to effect segregation of corresponding portions of the rod 1 (upon severing by the cutoff of the cigarette rod making machine) from the satisfactory articles. The remaining five radiation conducting units of the apparatus are indicated in FIG. 1 by arrows 17. Each such radiation conducting unit is associated with a discrete photoelectric transducer 14 as well as with a discrete light source 9. The outline of the beam of radiation which issues from the source 9 and passes through the collector lens 7 is shown at 9' on the partially light transmitting mirror 6 of FIG. 1. The lines 13 denote the outline of the reflected light beam, namely of that portion of reflected radiation which is permitted to pass through the slot 12 of the diaphragm 11 on its way toward the collector lens 8 and transducer 14. Each of the light beams 9' is designed to be reflected by a selected arcuate portion of the exterior of the wrapper 2 of the moving cigarette rod 1. One such selected portion is indicated in FIG. 1, as at 16. It is clear that the number of radiation conducting units, the number of transducers and the number of light sources can be reduced to less than six or increased above six without departing from the spirit of the invention.

It will be noted that each beam of radiation which is furnished by the respective source 9 is concentrated upon a relatively small portion 16 of the exterior of the wrapper 2. This contributes to sensitivity of the improved scanning apparatus. It will further be understood that it is not necessary to scan the entire exterior of the wrapper 2. For example, in certain cigarette rod making machines, it suffices to scan that portion of the wrapper which is provided with a seam as a result of overlapping and bonding of marginal portions of a web of cigarette paper to each other. A second unit can be provided in the region where the imprints are normally applied to the wrapper 2 so as to ascertain whether or not the imprints are present as well as whether or not the shade, tone or color of the imprints is satisfactory. The construction of each of the six radiation conducting units in the apparatus of FIGS. 1 and 2 is preferably the same.

An advantage of the utilization of a rod guide 3 which is assembled of flat plates is that reflection losses due to the passage of light from the source 9 toward the exterior of the wrapper 2 and due to passage of reflected light from the exterior of the wrapper 2 to the corresponding transducer 14 are reduced to a minimum. The illustrated polygonal rod guide 3 can be replaced with a ring-shaped guide having cylindrical internal and external surfaces without departing from the spirit of the invention. This would somewhat increase reflection losses as a result of passage of reflected light through the arcuate portions of the ring-shaped rod guide. However, a ring-shaped guide can be manufactured at a lower cost.

Figure 3:
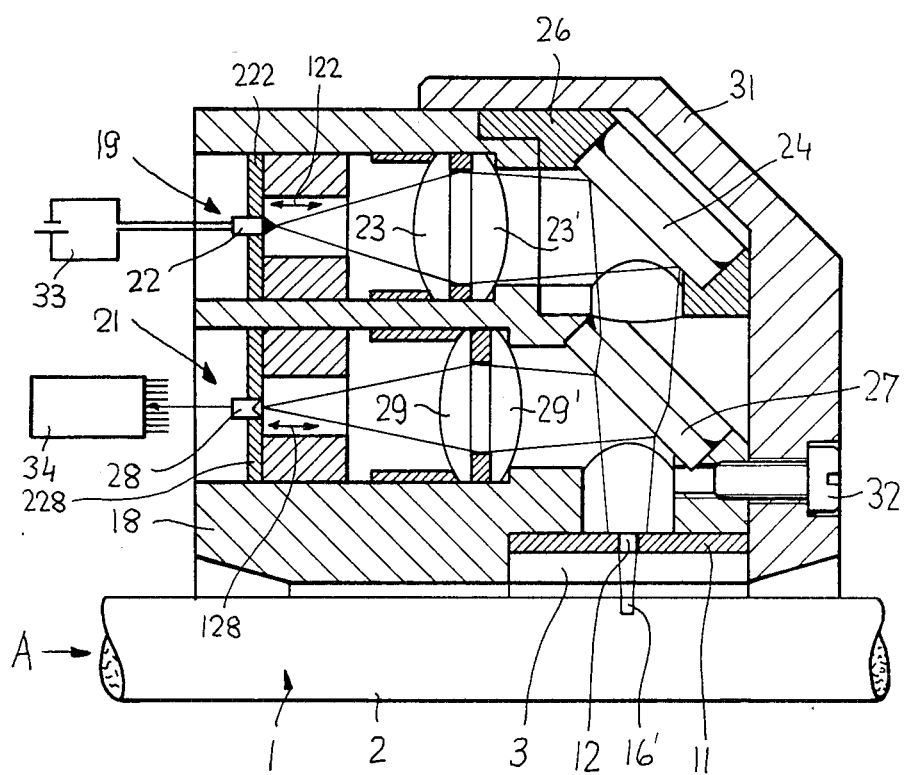
FIG. 3 is a fragmentary axial sectional view of a presently preferred embodiment of the improved apparatus.

Referring now to FIG. 3, there is shown a portion of an optical scanning or monitoring apparatus which embodies a presently preferred design of radiation conducting units. Only one such unit is actually shown; however, it will be understood that several (for example six) such units are or can be placed around a predetermined portion of the path for the moving cigarette rod 1. The apparatus comprises the aforementioned ring-shaped carrier 18 which defines an axial passage for the rod 1 and supports the rod guide 3. The latter can be constructed in the same way as shown in FIG. 1 or 2, i.e., it can comprise six flat plates 4 which surround a predetermined portion of the path for the rod 1 and permit passage of radiation from a source 22 to the exterior of the wrapper 2 of the rod 1 as well as the passage of reflected light from the exterior of the wrapper 2 to the transducer 28 of the unit which is actually shown in FIG. 3. Alternatively, and as already mentioned above, the illustrated polygonal rod guide 3 can be replaced with a ring-shaped rod guide having cylindrical internal and external surfaces.

The carrier 18 is formed with axially parallel bores 19 and 21 which are disposed at different distances from the path for the rod 1. There are six equidistant bores 21 and six equidistant bores 19; however, only one each of these bores is actually shown in FIG. 3. The bore 19 contains the radiation source 22 and lenses 23 and 23'. The source 22 is installed on the common optical axis of the lenses 23, 23' as well as in their focal point. The radiation conducting unit which is shown in FIG. 3 further comprises a totally reflecting mirror 24 which is disposed behind the lens 23' and serves to deflect radiation issuing from the source 22 in a direction radially of and at right angles to the axis of the moving rod 1. The totally reflecting mirror 24 is installed in a ring-shaped holder 26 and is preferably adjustable, together with this holder, relative to the carrier 18.

A portion of radiation which is totally reflected by the mirror 24 passes through a partially transmitting mirror 27 before it reaches the respective plate 4 of the rod guide 3 on its way toward the corresponding section or portion 16' of the exterior of the wrapper 2 forming part of the rod 1. The partially transmitting mirror 27 is installed in the carrier 18. As mentioned above, a portion of radiation (e.g., visible light) which is totally reflected by the mirror 24 passes through the mirror 27 on its way toward the exterior of the wrapper 2 of the rod 1, and such radiation passes through the slot 12 of the corresponding diaphragm 11 which is also installed in the carrier 18 outwardly of the corresponding plate 4 of the guide 3.

The bore 21 of the carrier 18 accommodates the corresponding transducer 28 as well as two lenses 29, 29'. The transducer 28 is located on the common optical axis of the lenses 29, 29' and in their focal point. The inclination of the partially transmitting mirror 27 is such that radiation which is reflected by the exterior of the wrapper 2 of the moving rod 1 and passes radially outwardly through the slot 12 of the corresponding diaphragm 11 is reflected by the mirror 27 toward the lenses 29', 29 and thence against the transducer 28. Such reflected radiation is focused upon the transducer 28. The construction of the radiation conducting unit including the lenses 23, 23', 29, 29' and mirrors 24, 27 is such that its optical axis extends radially of and is normal to the axis of the rod 1. This eliminates or greatly reduces the likelihood of inaccurate measurements as a result of development of shadows which are attributable to the presence of folds, undulations or other acceptable irregularities in the material of the wrapper 2. As mentioned above, the development of such shadows is especially pronounced if the incident radiation impinges against the exterior of the rod at an oblique angle as disclosed in the aforementioned U.S. Pat. No. 4,350,170. Furthermore, the improved apparatus is highly sensitive to defects which are sufficiently pronounced to warrant segregation of corresponding sections (plain cigarettes) of the rod 1 from satisfactory sections. The provision of a reasonable or substantial number of radiation conducting units as well as of an equal number of radiation sources and tranducers also contributes to greater sensitivity and reliability of the improved optical scanning apparatus.

The apparatus which is shown in FIG. 3 further comprises a cupped cover or lid 21 which overlies the lenses and mirrors to shield them from dust and other contaminants and is secured to the carrier 18 by screws 32 (only one shown) or analogous fasteners.

The radiation sources 22 are connected to a common source 33 of electrical energy. The outputs of all transducers 28 are connected to an evaluating circuit 34 a presently preferred construction of which is shown in FIG. 4.

Figure 4:
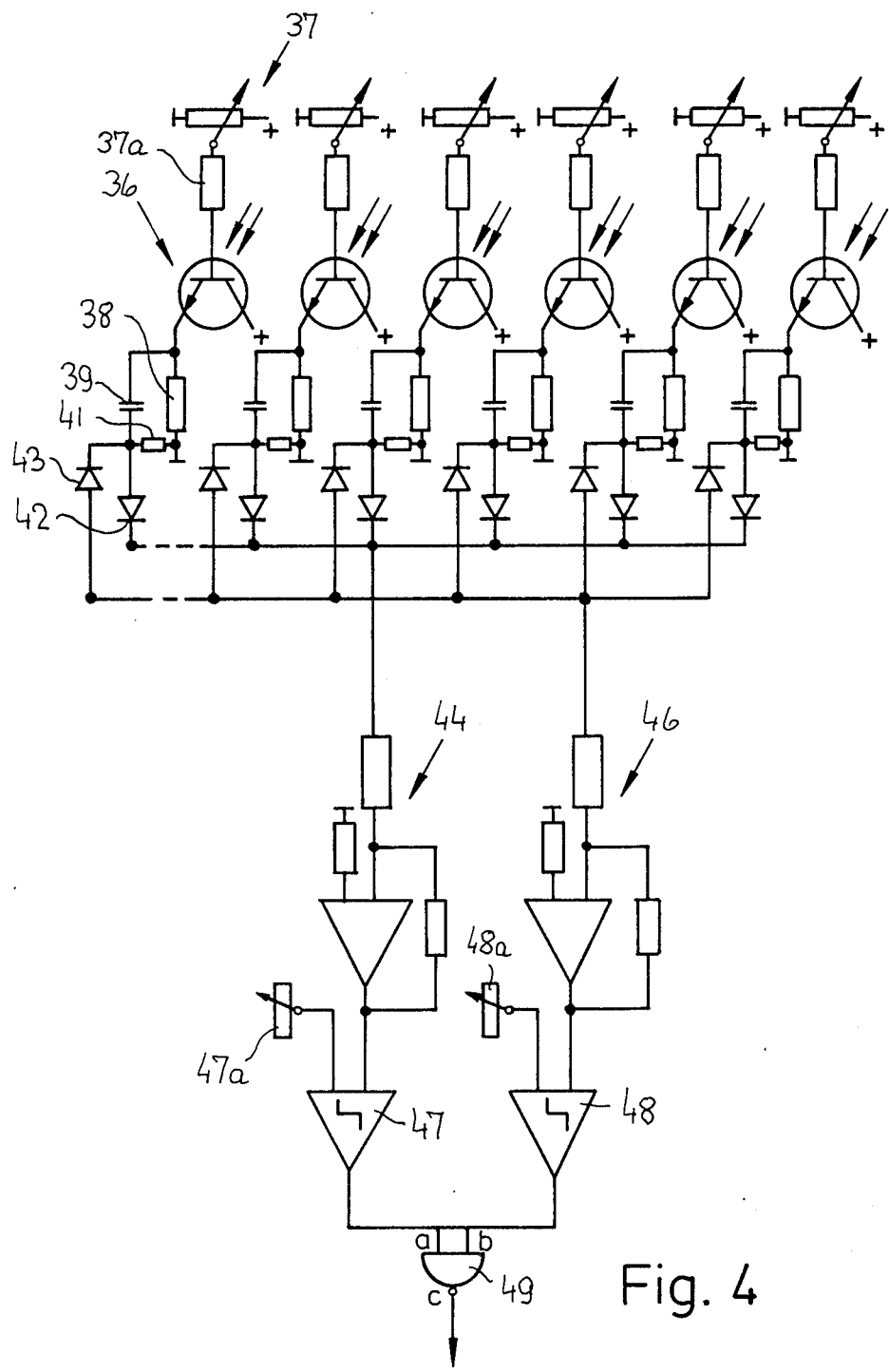
FIG. 4 is a circuit diagram of an evaluating system for signals which are generated by the transducers of the improved scanning apparatus.

Referring to FIG. 4, the evaluating circuit 34 which is shown therein is similar to the circuit shown in FIG. 3 of the aforementioned U.S. Pat. No. 4,350,170. It comprises phototransistors 36 each of which can be used as one of the transducers 14 or 28. Such phototransistors are connected with adjustable potentiometers 37 which allow for selection of their operating points by way of resistors 37a. Furthermore, each of the phototransistors 36 is connected with a load resistor 38, a capacitor 39 in parallel with the resistor 38, a discharge resistor 41 for the respective capacitor 39 as well as with a diode 42 for positive "bright" signals which are generated in response to detection of increased reflection of incident radiation and a diode 43 for negative or "dark" signals which are transmitted in the opposite direction and are generated in response to more pronounced absorption of light by the wrapper 2 of the cigarette rod 1. All of the diodes 42 are connected to a first operational amplifier 44, and all of the diodes 43 are connected to a second operational amplifier 46. The outputs of the amplifiers 44, 46 are respectively connected to the corresponding inputs of comparators 47, 48 whose outputs are connected to the corresponding inputs a, b of an OR gate 49. The output c of the gate 49 can transmit signals to an ejector for defective cigarettes. A suitable ejector is disclosed, for example, in commonly owned U.S. Pat. No. 3,914,989 granted Oct. 28, 1975 to Reuland.

If a beam of radiation issuing from one of the sources 22 impinges upon a bright portion of thewrapper 2 of the moving cigarette rod 1, for example, upon a spot of adhesive which should not be present at the exterior of the wrapper, the adhesive spot causes a more pronounced reflection of incident radiation so that the corresponding phototransistor 36 transmits a signal of different (greater) intensity. The increased intensity of the signal which is transmitted by such phototransistor initiates the discharge of the corresponding capacitor 39 and the flow of a current through the respective diode 42 to the input of the operational amplifier 44 which reacts to more pronounced "bright" signals. If the itensity of signal that is transmitted to the amplifier 44 exceeds the threshold value which is selected by a potentiometer 47a for the corresponding comparator 47, the output of this comparator transmits a signal to the input a of the OR gate 49 whereby the output c of the OR gate transmits a signal to the ejector which segregates the corresponding plain cigarette from satisfactory cigarettes downstream of the aforementioned cutoff in the cigarette rod making machine.

If the beam of radiation which is transmitted by one of the sources 22 and reaches the exterior of the wrapper 2 happens to impinge upon a dark portion of the rod, for example, upon tobacco shreds which are accessible to the beam through a hole in the wrapper 2, the intensity of signal which is transmitted by the corresponding phototransistor 36 is reduced whereby the associated diode 43 transmits a signal to the amplifier 46 which transmits a signal to the corresponding input of the comparator 48. If the intensity of such signal is below that which is selected by a potentiometer 48a, the output of the comparator 48 transmits a signal to the input b of the OR gate 49 whereby the output c of this gate transmits a signal to the ejecting mechanism so that the plain cigarette exhibiting a hole in its wrapper is segregated from other cigarettes. In such instance, a drop of intensity of the voltage signal which is transmitted by the corresponding phototransistor 36 entails a discharge of the associated capacitor 39 with the result that a current flows through the corresponding diode 43 to the input of the amplifier 46.

The presence or absence of open seams (dark spots), the presence or absence of imprints (dark or bright spots) or improper application of imprints is detected in an analogous manner.

The rod guide 3 can be made of glass whose surfaces are preferably treated in a suitable way so as to reduce reflection. The partially transmitting mirrors 6 and 27 are preferably constructed in such a way that they transmit half of incident radiation and reflect half of reflected radiation. However, it is also possible to utilize mirrors which are constructed in such a way that they reflect a higher percentage of radiation and transmit a smaller percentage of incident radiation. This means that, in the embodiment of FIG. 3, a higher percentage of light issuing from the source 22 will be reflected by the mirror 27 and will be lost for the purposes of scanning the exterior of the moving rod 1. This can be compensated for by selecting a radiation source which is capable of emitting radiation of greater intensity. On the other hand, such construction of the mirror 27 ensures that a higher percentage of reflected radiation reaches the transducer 28 so that the apparatus is capable of more reliably detecting the presence of defects at the exterior of the wrapper 2. In other words, one can optimize the sensitivity of the improved apparatus by selecting mirrors 27 which reflect a higher percentage of radiation and transmit a lower percentage of incident radiation.

The arrow 122 denotes in FIG. 3 the directions in which the radiation source 22 is preferably adjustable (for example, with its support 222) along the common optical axis of the lenses 23 and 23'. Analogously, the transducer 28 is preferably adjustable along the common optical axis of the lenses 29, 29' together with or relative to its support 228. The directions of shiftability of the transducer 28 are indicated by a double-headed arrow 128. Such adjustability of the sources 22 and transducers 28 relative to the carrier 18 renders it possible to effect a highly accurate calibration of the optical scanning apparatus. It is equally possible to shift the lenses 23, 23' and 29, 29' relative to the carrier 18, again along the optical axes of such lenses.

The provision of a carrier 18 with a rod guide 3 therein and a cover 31 thereon reduces the likelihood of rapid contamination of the components of the radiation conducting units in the improved apparatus. The likelihood of contamination with dust and/or other solid contaminants is especially pronounced in cigarette rod making or filter rod making machines.

As mentioned above, a relatively cheap rod guide can be constructed in the form of a hollow cylindrical sleeve with cylindrical internal and external surfaces. However a rod guide which has a polygonal cross-sectional outline and consists of several flat plates 4 is preferred at this time because the losses due to reflection of radiation by the rod guide are reduced to a minimum.

The provision of radiation conducting units which comprise beam splitters is advisable and advantageous because this ensures that not only the incident radiation but also the reflected radiation can pass radially of and at right angles to the axis of the moving rod 1. Each of the aforediscussed partially transmitting mirrors 6 and 27 constitutes a beam splitter.

While it is possible to distribute the several radiation conducting units at unequal intervals around a selected portion of the path for the moving rod 1, the placing of such units at equal angular distances from one another is preferred at this time. The provision of diaphragms 11 is desirable in order to reduce the likelihood of undesirable influencing of transducers 14 or 28 by radiation passing through the neighboring radiation conducting unit or units.

An important advantage of the improved optical scanning apparatus is that it is capable of reliably detecting all such defects of the wrapper 2 which are sufficiently serious to warrant segregation of corresponding plain cigarettes or filter rod sections from satisfactory cigarettes or filter rod sections. Furthermore, and as explained above, the provision of radiation conducting units which direct radiation radially of and at right angles to the axis of the moving rod reduces the likelihood of excessive sensitivity of the apparatus to the presence of undulations, folds or similar irregularities in the wrapper of the rod which may detract somewhat from the appearance of the ultimate product but do not affect its quality.

Another important advantage of the improved apparatus is that it comprises several radiation conducting units which are distributed around the path of the moving rod 1. This enables the apparatus to simultaneously detect a wide variety of defects as well as to classify such defects according to their nature and location, for example, whether or not they are caused by excessive or insufficient reflection of incident radiation. The provision of discrete radiation sources and the provision of signal generating means consisting of a plurality of discrete transducers also contributes to reliability and reproducibility of measurements. It has been found that the improved apparatus is capable of accurately and reliably detecting all kinds of defects which are undesirable to the manufacturer of rod-shaped smokers' articles and/or to the purchaser of such commodities. Signals which are generated by the improved apparatus are sufficiently pronounced so as to allow for convenient regulation of the operation of the machine which turns out the rod and/or for reliable segregation of corresponding (defective) rod-shaped articles. The sensitivity of the improved apparatus is further enhanced if the rod guide 3 consists of or comprises flat plates which are disposed in such a way that radiation passing at right angles therethrough extends radially of and at right angles to the axis of the moving rod. The provision of suitable lenses and mirrors as constituents of the radiation conducting units allows for predictable and desirable concentration of radiation issuing from the radiation admitting means upon the corresponding sections of the exterior of the wrapper 2 as well as proper focusing of reflected radiation upon the constituents of the signal generating means. This also contributes to higher sensitivity of the improved apparatus.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. Apparatus for optically scanning the exterior of cigarette rods and analogous rod-shaped products of the tobacco processing industry which move lengthwise along a predetermined path, comprising a plurality of radiation conducting units at least partially surrounding a portion of said path and arranged to conduct radiation substantially radially inwardly toward and at right angles to the axis of the rod; an annular carrier for said units, said carrier surrounding the rod in said portion of said path; means for admitting radiation to said conducting units so that such radiation is directed against the corresponding portions of the exterior of the moving rod and is reflected back into the respective units, the characteristics of reflected radiation being indicative of the condition of the corresponding portion of the exterior of the rod; means for generating signals denoting the characteristics of reflected radiation; and a light-transmitting rod guide provided in said carrier and interposed between said units and the rod in said portion of said path so that radiation issuing from said admitting means as well as radiation which is reflected by the exterior of the rod passes through said guide, said guide including a radiation transmitting plate for each of said units, said plates together constituting a polygonal sleeve and being disposed in planes extending at right angles to the direction of propagation of radiation from the respective units to the corresponding portions of the exterior of the rod in said path and the direction of propagation of reflected radiation back to the respective units.

2. The apparatus of claim 1, wherein said units form an annulus around the rod in said portion of said path.

3. The apparatus of claim 1, wherein said radiation admitting means comprises at least one radiation source and said signal generating means comprises at least one optoelectrical transducer.

4. The apparatus of claim 1, wherein each of said units comprises at least one mirror and at least one lens.

5. The apparatus of claim 1, wherein said radiation admitting means comprises at least one light source.

6. The apparatus of claim 1, wherein each of said units includes at least one mirror and at least one lens, said signal generating means comprising a discrete photoelectrical transducer for each of said units.

7. The apparatus of claim 1, wherein said admitting means includes means for admitting a beam of radiation to each of said units and each of said units includes beam splitting means arranged to direct a portion of the respective beam against the exterior of the rod in said portion of said path and a portion of reflected radiation against the signal generating means.

8. The apparatus of claim 7, wherein each of said beam splitting means comprises a partly transmitting mirror.

9. The apparatus of claim 1, wherein each of said units comprises a totally reflecting mirror arranged to direct radiation from said admitting means substantially radially toward the exterior of the rod in said path and a partially transmitting mirror disposed in the path of radiation from said totally reflecting mirror and arranged to direct a portion of reflected radiation toward said signal generating means.

10. The apparatus of claim 9, wherein said units are uniformly distributed around the rod in said portion of said path and said radiation-transmitting rod guide is installed in said carrier between said partially transmitting mirrors and said portion of said path.

11. The apparatus of claim 9, wherein said admitting means comprises a discrete radiation source for each of said units and said signal generating means comprises a discrete transducer for each of said units.

12. The apparatus of claim 1, further comprising diaphragms, one for each of said units, for controlled transmission of radiation from said admitting means to the exterior of the rod in said path and for controlled transmission of reflected radiation to said signal generating means.

13. The apparatus of claim 1, wherein said admitting means comprises a discrete radiation source for each of said units and each of said units has an optical axis, said sources being movable along the optical axes of the respective units.

14. The apparatus of claim 13, wherein said sources are adjustably mounted in said carrier.

15. The apparatus of claim 1, wherein said signal generating means comprises a discrete transducer for each of said units and each of said units has an optical axis, said transducers being adjustable along the optical axes of the respective units.

16. The apparatus of claim 15, wherein said transducers are adjustably mounted in said carrier.

* * * * *